United States Patent [19]

Sessler et al.

[11] Patent Number: 5,120,411

[45] Date of Patent: Jun. 9, 1992

[54] PHOTODYNAMIC ACTIVITY OF SAPPHYRINS

[75] Inventors: Jonathan L. Sessler; Anthony Harriman, both of Austin, Tex.; Bhaskar G. Maiya, Hyderabad, India

[73] Assignee: Board of Regents, The University of Texas System, Austin, Tex.

[21] Appl. No.: 454,301

[22] Filed: Dec. 21, 1989

[51] Int. Cl.[5] .................. C07D 487/22; C07F 5/00
[52] U.S. Cl. .................. 204/157.15; 204/157.61
[58] Field of Search .................. 204/157.61, 157.15

[56] References Cited

U.S. PATENT DOCUMENTS

| | | | |
|---|---|---|---|
| 4,883,790 | 11/1989 | Levy et al. | 540/145 |
| 4,915,683 | 5/1990 | Sieber | 604/4 |
| 4,935,498 | 6/1990 | Sessler et al. | 534/15 |

FOREIGN PATENT DOCUMENTS

| | | |
|---|---|---|
| 0111418 A2 | 6/1984 | European Pat. Off. . |
| 0196515 A1 | 10/1986 | European Pat. Off. . |
| 0233701 A2 | 8/1987 | European Pat. Off. . |

OTHER PUBLICATIONS

PCT Search Report, mailed 2 Aug. 1990.
Harriman et al., J. Chem. Soc., Chem. Commun., (1989) 314–316.
Sessler et al., Chem. Absts., vol. 111:125716e (2 Oct. 1989).
Sessler et al., J. Amer. Chem. Soc., 110(16):5586–5588 (1988).

Primary Examiner—John F. Niebling
Assistant Examiner—Isabelle R. McAndrews
Attorney, Agent, or Firm—Arnold, White & Durkee

[57] ABSTRACT

The present invention includes a method to produce singlet oxygen from molecular oxygen generated by reaction with a sapphyrin compound excited at an absorbing wavelength to form a triplet species. Specifically, the sapphyrin compound is an alkylated sapphyrin, most preferably diprotonated 3,8,12,13,17,22-hexaethyl-2,7,18,23-tetramethylsapphyrin. Generation of the triplet species may be accomplished in an organic solvent, of which the most preferable solvents are chloroform, methanol or acetonitrile.

Also encompassed within the present invention is a method to selectively produce singlet oxygen in an aqueous environment. A sapphyrin compound is incorporated within a membranous vesicle, the vesicle is illuminated with exciting light and the resultant excited triplet state sapphyrin compound reacts with molecular oxygen to produce singlet oxygen. Singlet oxygen was not generated external to the vesicle where the sapphyrin compound is present in an aqueous medium.

18 Claims, 7 Drawing Sheets

FIGURE 1

δ, ppm

FIGURE 2a

δ, ppm

FIGURE 2b

δ, ppm

PHOTODYNAMIC ACTIVITY OF SAPPHYRINS

This application is a continuation-in-part of the co-pending application, U.S. Ser. No. 07/320,293, filed Mar. 6, 1989, now U.S. Pat. No. 4,935,498, issued June 19, 1990.

BACKGROUND OF THE INVENTION

This application relates to two other patent applications filed on an even date herewith: SAPPHYRINS, DERIVATIVES, AND SYNTHESES (by Sessler and Cyr Ser. No. 07/454,298) and PHOTODYNAMIC VIRAL DEACTIVATION WITH SAPPHYRINS (by Matthews, Sessler, Judy, Newman and Sogandares-Bernal Ser. No. 07/454,300).

The present invention relates to a photochemical method of producing singlet oxygen using sapphyrin compounds to generate a triplet excited state species which then interacts with molecular oxygen The resultant singlet oxygen is highly reactive and is potentially useful for a variety of medical applications. Discovery of the sapphyrin molecules as photosensitizers for singlet oxygen production appears likely to lead to efficient, localized, and selective in vivo therapy, especially in the emerging field of photodynamic tumor or viral therapy.

Investigations relating to the present invention were supported by Texas Advanced Research Program grant number 1581 and by the Biotechnology Resources Program of the NIH (RR 008866).

Figure 1:
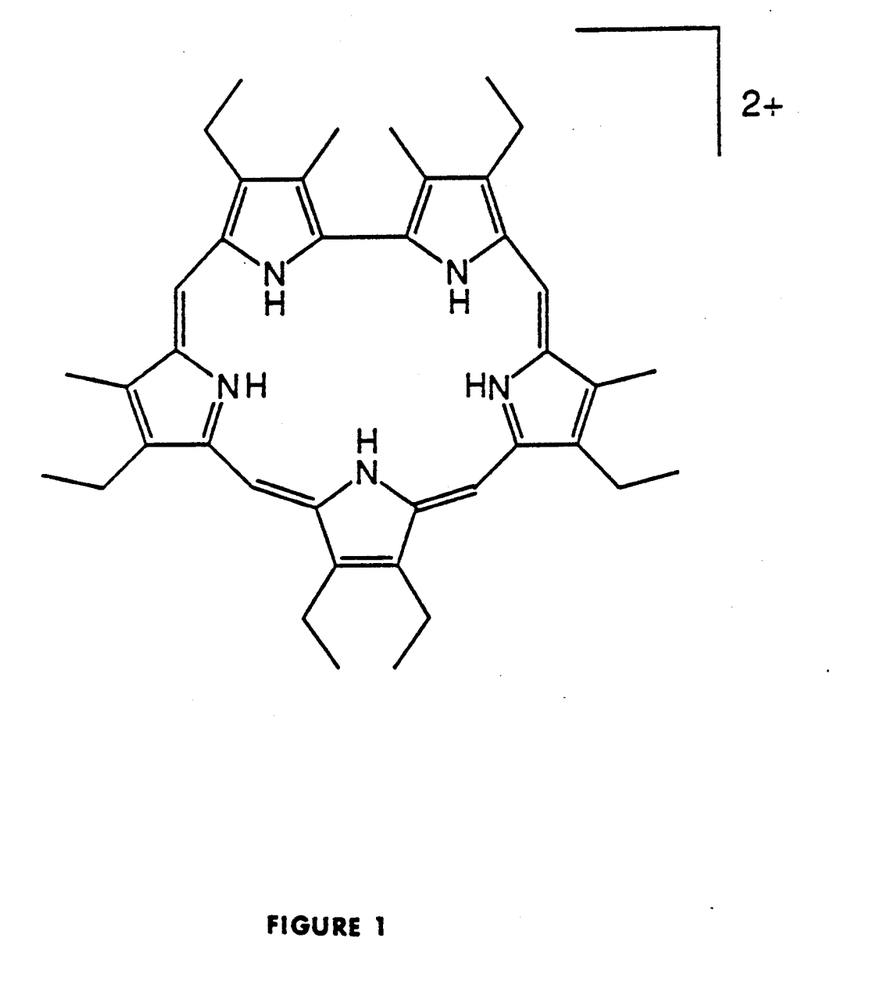
FIG. 1 shows the structure of the diprotonated sapphyrin conjugate diacid ($SAP^{2+}$) derivative used in this work.

Macrocyclic ligands capable of complexing metal cations are finding an increasing number of applications in biomedical research, most specifically as photosensitizers in photodynamic therapy and as targets for magnetic resonance imaging processes. One approach to extending the range of compounds available for such studies involves the use of expanded porphyrins in which the basic ring structure is enlarged beyond the normal 18 $\pi$-electrons periphery. Recently, the "texaphyrin" family of expanded porphyrins was introduced and shown to have useful photosensitizing properties ((a) Sessler, J. L.; Murai, T.; Lynch, V.; Cyr, M. *J. Am. Chem. Soc.* 1988, 110, 5586: (b) Sessler J. L.; Murai T.; Lynch, V. *Inorg. Chem.* 1989, 28, 1333: (c) Harriman, A.; Maiya, B. K.; Murai, T.; Hemmi, G.; Sessler, J. L.; Mallouk, T. E. *J. Chem. Soc., Chem. Commun.* 1989, 314: (d) Maiya, B. K.; Harriman, A.; Sessler, J. L.; Hemmi, G.; Murai, T.; Mallouk, T. E. *J. Phys. Chem.* in press). This work is now extended to include "sapphyrin", a pentapyrrolic 22 $\pi$-electron "expanded porphyrin" first prepared by the groups of Johnson and Woodward (Reported by R. B. Woodward at the Aromaticity Conference, Sheffield, U.K. 1966) a number of years ago but essentially unexplored in the years since ((a) Broadhurst, M. J.; Grigg, R. *J. Chem. Soc., Perkin Trans.* 1 1972, 2111; (b) Bauer, V. J; Clive, D. L. J.; Dolphin, D.; Paine III, J. B.; Harris, F. L.; King, M. M.; Lodger, J.; Wang, S.-W. C.; Woodward, R. B. *J. Am. Chem. Soc.* 1983, 105, 6429). The sapphyrins possess two properties which make them of potential interest for biomedical applications: First, they contain an unusually large central cavity which could provide an effective means of complexing large lanthanide cations for use in magnetic resonance imaging. Second, they absorb light strongly at a wavelength of about 680 nanometer (nm). The present invention relates to the synthesis of a sapphyrin molecule and investigation of its photophysical properties in various solvents. The most stable form of sapphyrin under such conditions is the diprotonated conjugate diacid (SAP$^{2+}$) in which all five N-atoms are protonated and we have concentrated on this molecule, the structure of which is given in FIG. 1.

In a parallel study (Judy, M. M.; Mathews, J. L.; Boriak, R.; Skiles, H.; Cyr, M.; Maiya, B.G.; Sessler, J. L. *Photochem. Photobiol.* to be submitted), the present inventors have found that SAP$^{2+}$ acts as an effective in vitro agent for the photodynamic inactivation (PDI) of herpes simplex virus (HSV). At a SAP$^{2+}$ concentration of 60 $\mu$M and with a light intensity of 10 J cm$^{-2}$, a five logarithm killing of HSV is effected under conditions where little or no dark activity is detected. Singlet oxygen, directly or indirectly, appears to be the inactivating agent.

PDI-based purifications also appear to lend themselves to ex vivo photosensitized blood purification procedures. One method would be to generate matrix-supported PDI sapphyrin systems. A sapphyrin molecule would be attached to a solid matrix, such as polystyrene beads. Blood would then be irradiated, for example, while being passed through the sapphyrin-coated beads. Clearly, beads which do not absorb in the 680–730 nm range should be used since the sapphyrin compounds absorb in the 680–690 nm region. Carboxylated sapphyrins might be good candidates for attachment to amino-functionalized matrices. For example, sapphyrin 2 could be converted to an acid chloride after partial ester hydrolysis, then reacted with a pendant amino group (e.g., aminomethylated partially cross-linked Merrifield-type polystyrene) to form an amide linkage to the matrix.

SUMMARY OF THE INVENTION

The present invention includes a method to produce singlet oxygen from molecular oxygen generated by reaction with a sapphyrin compound excited at an absorbing wavelength to form a triplet species. Specifically, the sapphyrin compound is an alkylated sapphyrin, most preferably diprotonated 3,8,12,13,17,22-hexaethyl-2,7,18,23-tetramethylsapphyrin. Generation of the triplet species may be accomplished in an organic solvent, of which the most preferable solvents are chloroform, methanol, acetonitrile or similar solvents.

Also encompassed within the present invention is a method to selectively produce singlet oxygen in an aqueous environment. A sapphyrin compound is incorporated within a membranous vesicle, the vesicle is illuminated with exciting light and the resultant excited triplet state sapphyrin compound reacts with molecular oxygen to produce singlet oxygen. Singlet oxygen was not generated external to the vesicle where the sapphyrin compound is present in an aqueous medium.

The present invention further includes a means to moderate the production of singlet oxygen in an organic solvent. This involves adding to the solution in which singlet oxygen is being generated an appropriate amount of a protein such as serum albumin or a membranous material such as a liposome to which the sapphyrin compound will bind. The reaction between molecular oxygen and the bound sapphyrin compound in the presence of exciting light is greatly diminished.

BRIEF DESCRIPTION OF THE DRAWINGS

FIGS. 2a, 2b and 2c show the portions of the $^1H$-nmr spectra of $SAP^{2+}$ as recorded in different solvents (FIG. 2a, $CDCL_3$; FIG. 2b, $CD_3OD$; and FIG. 2c, $CD_3CN$). The signals observed between 10 and 12 ppm and between $-4$ and $-12$ ppm are assigned to meso-H and pyrrolic N-H protons respectively.

DETAILED DESCRIPTION OF PREFERRED EMBODIMENTS

This invention demonstrates the generation of singlet oxygen from reaction of molecular oxygen with an excited state triplet species of a sapphyrin compound. This discovery demonstrates a safe and efficient photosensitizer for use in the photodynamic inactivation of envelope viruses such as HIV-1 and other pathogens in blood without harm to normal blood components.

The physical state of $SAP^{2+}$ depends markedly upon the environment. In organic solvents of low polarity, $SAP^{2+}$ exists as a monomer but with extensive ion-pairing with its $Cl^-$ counterions ((a) Austin, E.; Gouterman, M. Bioinorg. Chem. 1968, 90, 2735: (b) Harriman, A.; Richoux, M.—C. J. Photochem. 1984, 27, 205). Increasing the polarity of the solvent favors dissociation of the ion-pair and dimerization of the macrocycle, the dimer appearing to possess an ordered structure with partial overlap of $\pi$-electron systems. Interestingly, both monomer ion-pair and dimer exhibit similar photodynamic behavior and, upon illumination with visible light in aerated solution, give rise to modest quantum yields for formation of $O_2(^1\Delta_g)$. However, in aqueous media $SAP^{2+}$. aggregates and deposits onto the surface of albumin and liposomes. These aggregates exhibit no useful photodynamic activity.

The in vivo photodynamic properties of $SAP^{2+}$ will depend, therefore, upon its site of localization. In a non-polar membrane, such as found in mitochondria, $SAP^{2+}$ should exist as a monomer ion-pair and be capable of producing $O_2(^1\Delta_g)$ at modest rates upon illumination under aerobic conditions. Localizing $SAP^{2+}$ at a more polar site, perhaps near an interface, will favor dimerization of the macrocycle but this will not affect its photodynamic activity. Any $SAP^{2+}$ that resides in the aqueous phase will aggregate onto the surface of serum albumin or intact cells and will be photochemically inert. Thus, photodynamic action appears restricted to the inside of cells and membranes. This is a useful property for a photosensitizer, especially if it can be allied to selective incorporation into infected cells, since it ensures minimum destruction of the transporting proteins. The other useful property shown by $SAP^{2+}$ that has not been clearly demonstrated for any tetrapyrrolic macrocycle is the similarity in photodynamic activity shown by monomer and dimer species. Of course, the extent of $\pi,\pi$ interaction and, particularly, the exciton coupling energy depends upon the mutual separation distance and orientation of the two macrocycles within the dimer (Gouterman, M.; Holten, D.; Lieberman, E. Chem. Phys. 1977, 25, 39). Since the medium will affect such parameters, it is possible that the photodynamic activity of the dimer will show a pronounced dependence upon the environment. These studies provide a background for the understanding of the high in vitro photodynamic inactivation (PDI) activity (Judy, M. M.; Mathews, J. L.; Boriak, R.; Skiles, H.; Cyr, M.; Maiya, B. G.; Sessler, J. L. Photochem. Photobiol. to be submitted) of this hitherto little studied system.

The following procedures, preparations, and analytical methods were employed in the determination and use of the present invention.

Materials 3,8,12,13,17,22-Hexaethyl-2,7,18,23-tetramethylsapphyrin (SAP) was prepared using an improvement of the general method of Bauer et al. (Bauer et al. J. Am. Chem. Soc. 1983, 105, 6429) and purified by extensive column chromatography. It was converted into the more stable conjugate diacid $SAP^{2+}$ by treatment with dilute HCl. Solvents were spectroscopic grade and were used as received. Human serum albumin was obtained from Sigma Chem. Co. and defatted according to the method of Chen (Chen, R. F. J. Biol. Chem. 1967, 242, 173). Aliquots of albumin in water at pH 7 containing 0.01 M NaCl were titrated with solutions of $SAP^{2+}$ in $CH_3OH$ and the treated albumin solutions were dialyzed against neutral aqueous NaCl solution. Liposomes were prepared by the general method of Jori et al.(Jori, G.; Tomio, L.; Reddi, E.; Rossi, E.; Corti, L.; Zorai, P. L.; Calzavara, F. Br. J. Cancer 1983, 48, 307). For the positively-charged liposomes, an ethanol solution (5 $cm^3$) containing L-α-phosphatidyl choline (egg yolk) (63 μmols), stearylamine (18 μmols) and cholesterol (9 μmols) was purged continuously with $N_2$ while the ethanol was slowly evaporated. Water (5 $cm^3$) at pH 7.2 (2 mM) phosphate buffer was added and the mixture vortexed for 5 mins at 10° C. Aliquots of an ethanol solution of $SAP^{2+}$ were injected and the ethanol removed by purging with $N_2$. The mixture was then vortexed for a further 5 minutes and homogenized in a sonicator for 20 mins. Negatively-charged liposomes were prepared similarly except that diacetylphosphate was used in place of stearylamine.

Absorption Spectra

Absorption spectra were recorded with a Hewlett-Packard 8450A diode array spectrophotometer and fluorescence spectra were recorded with a Perkin-Elmer LS5 spectrofluorimeter. Fluorescence spectra were fully corrected for the instrumental response (Argauer, R. J.; White, C. E. Anal. Chem. 1964, 36, 368) and fluorescence quantum yields were calculated with respect to tetraphenylporphyrin ($H_2TPP$) in benzene (Brookfield, R. L.; Ellul, H.; Harriman, A.; Porter, G. J. Chem. Soc., Faraday Trans. 2 1986, 82, 219) after making corrections for changes in refractive index (Nakashima, N.; Meech, S. R.; Auty, A. R.; Jones, A. C.; Phillips, D. J. Photochem. 1985, 30, 207). Singlet excited state lifetimes were measured by the time-correlated single photon counting technique using a mode-locked, synchronously-pumped, cavity-dumped dye laser (lambda = 590 nm, time resolution 280 ps) as excitation source (O'Connor, D. V.; Phillips, D. "Time Correlated Single Photon Counting" Academic Press: London, 1984).

Flash Photolysis

Flash photolysis studies were made with a Q-switched, frequency-doubled (lambda=532 nm, 280 mJ) or tripled (lambda=355 nm, 80 mJ) Quantel YG481 Nd-YAG laser (pulse 12 ns). The laser intensity was attenuated with neutral density filters. An averaging procedure was used to increase the signal-to-noise ration in which the signals from 30 laser pulses were averaged for each determination. The concentration of $SAP^{2+}$ in each solvent was selected to optimize the presence of monomer or dimer, as described in the text, and all solutions were purged thoroughly with $N_2$. Transient species were monitored by optical absorption spectroscopy, spectra being recorded point-by-point, using a pulsed high-intensity Xe arc as probing beam and a high radiance monochromator. Absorbance changes were recorded at a fixed wavelength and analyzed with a PDP 11/70 minicomputer. Difference molar extinction coefficients for the triplet excited state of $SAP^{2+}$ in each solvent were determined by the complete conversion method (Bensasson, R. V.; Land, E. J.; Truscott, T. G. "Flash Photolysis and Pulse Radiolysis: Contributions to the Chemistry of Biology and Medicine" Pergammon Press: Oxford, 1983) using high laser intensities. In each case, the laser intensity was varied over a wide range using metal screen filters and complete conversion was apparent from attainment of a plateau region. Triplet excited state quantum yields were measured with respect to zinc tetraphenylporphyrin in benzene, for which the molar extinction coefficient (Pekkarinen, L.; Linschitz, H. *J. Am. Chem. Soc.* 1960, 82, 2407) (e ) at 470 nm is 74,000 $M^{-1} cm^{-1}$ and the quantum yield for formation of the triplet excited state (Hurley, J. K.; Sinai, N.; Linschitz, N. *Photochem. Photobiol.* 1983, 38, 9) ($\Phi_t$) is 0.83.

Yields of $O_2(^1\Delta_g)$ were determined by monitoring its characteristic phosphorescence at 1270 nm using a Ge photodiode (Rodgers, M. A. J.; Snowden, P. T. *J. Am. Chem. Soc.* 1982, 104, 5541). Solutions of $SAP^{2+}$ or the reference compound in each solvent were matched to possess an identical absorbance at 355 or 532 nm within the range 0.05–0.25 and were saturated with $O_2$; at least 4 different absorbances being used for each set of experiments. The solutions were irradiated with single 12 ns pulses delivered with a frequency-doubled or tripled, Q-switched Quantel YG481 Nd-YAG laser. The energy of the laser was attenuated with metal screen filters and the observed $O_2(^1\Delta_g)$ luminescence intensity was measured as a function of laser power. For $CD_3OD$ solutions, free-base tetrakis(3-hydroxyphenyl)-porphyrin ($\Phi_\Delta = 0.57$) was used as reference material (Bonnett, R.; McGarvey, D. J.; Harriman, A.; Land, E. J.; Truscott, T. G.; Winfield, U.-J. *Photochem. Photobiol.* 1988, 48, 271) using both 355 and 532 nm laser excitation. The reference compound used for $CD_3CN$ solutions was benzophenone (Chattopadhyay, S. K.; Kumar, C. V.; Das, P. K. *J. Photochem.* 1985, 30, 81) ($\Phi_\Delta = 0.37$) with excitation at 355 nm whereas for $CD_2Cl_2$ solutions the ethyl ester of Rose Bengal ($\Phi_\Delta = 0.61$) was used as standard (Lamberts, J. J. M.; Neckers, D. C. *Tetrahedron* 1985, 41, 2183) with excitation at both 355 and 532 nm. In each case, 50 individual signals were averaged and analyzed with the PDP 11/70 minicomputer, the initial luminescence intensity being extrapolated to the center of the laser pulse by standard computer least-squares fitting procedures.

Spectroscopic Properties

The $^1$H-nmr spectrum of $SAP^{2+}$ in $CDCl_3$ solution showed well resolved peaks at 11.66 and 11.70 ppm (s, 4H, meso-H), 4.71 and 4.55 ppm (m, 12H, methylene-H) and 4.23, 4.12 and 2.25 ppm (s, 30H, methyl-H). The meso-H signals observed for $SAP^{2+}$ (FIG. 2) are ca. 1 and 0.6 ppm downfield compared to the corresponding signals for free-base octaethylporphyrin (Broadhurst, M. J.; Grigg, R.; Johnson, A. W. *J. Chem. Soc., Chem. Commun.* 1969, 1480) and the hydrofluoroacetate salt of diprotonated octamethylporphyrin (Bauer et al. *J. Am. Chem. Soc.* 1983, 105, 6429) respectively. Most probably these shifts relate to the larger ring size of the 22 $\pi$-electron $SAP^{2+}$ molecule relative to the 18 $\pi$-electron tetrapyrrolic macrocycles (Knübel, G.; Franck, B. *Angew. Chem. Int. Ed. Enol.* 1988, 27, 1170). Indeed, even larger downfield shifts have been reported (Janson, T. R.; Katz, J. J. "The Porphyrins" Dolphin, D. Ed. Academic Press: New York. 1979, Vol. IV. Chap. 1) for the peripheral protons of some 26 and 34 $\pi$-electron macrocycles. The spectrum recorded for $SAP^{2+}$ also shows three singlets upfield of TMS, located at −4.33, −4.66 and −4.99 ppm, which are assigned to the pyrrolic protons residing in the cavity in the center of the macrocycle (FIG. 2). The pattern observed for these latter resonances (2:1:2) indicates that the five central protons are non-equivalent, quite unlike the case observed with the corresponding tetrapyrrolic macrocycles (Janson, T. R.; Katz, J. J. "The Porphyrins" Dolphin, D. Ed. Academic Press: New York. 1979, Vol. IV. Chap. 1), under these conditions. This suggests that these central protons interexchange on slow time-scales, possibly because the increased cavity size keeps them spatially remote. The larger size of the $SAP^{2+}$ induces a further upfield shift in the central proton resonances than found in the corresponding porphyrin analogues.

Figure 2A:
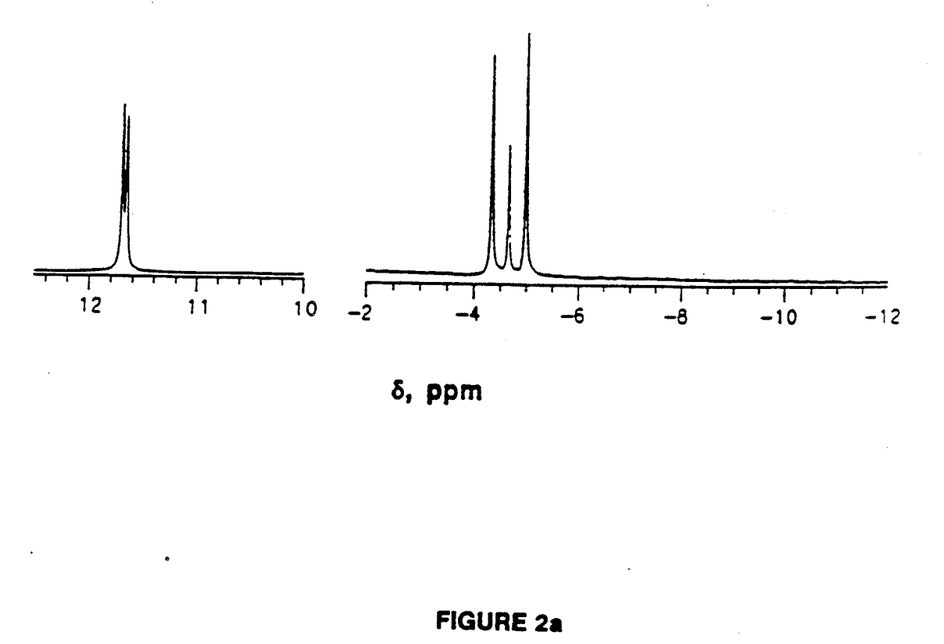
Figure 2B:
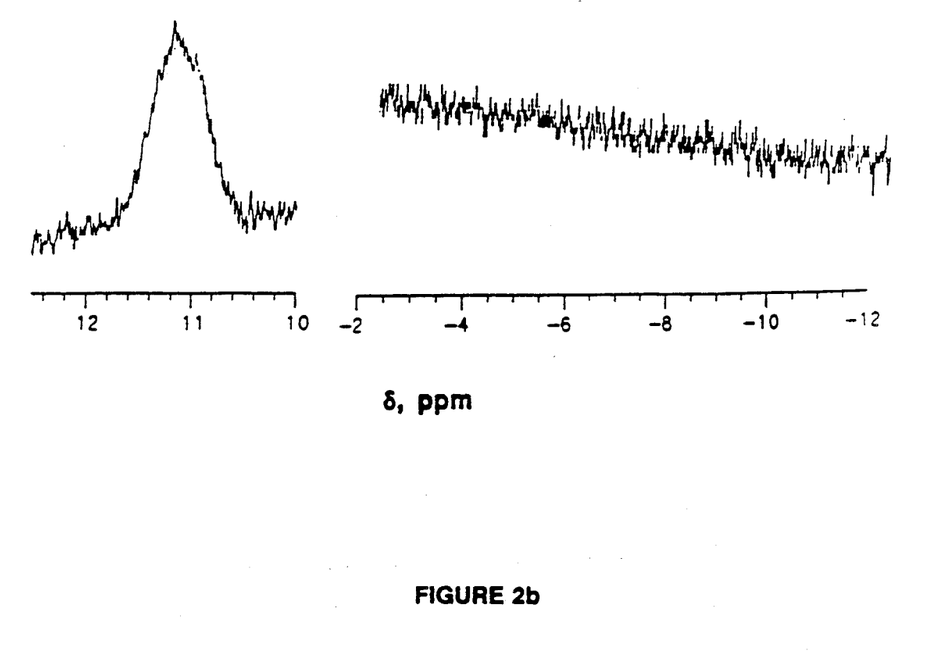
Figure 2C:
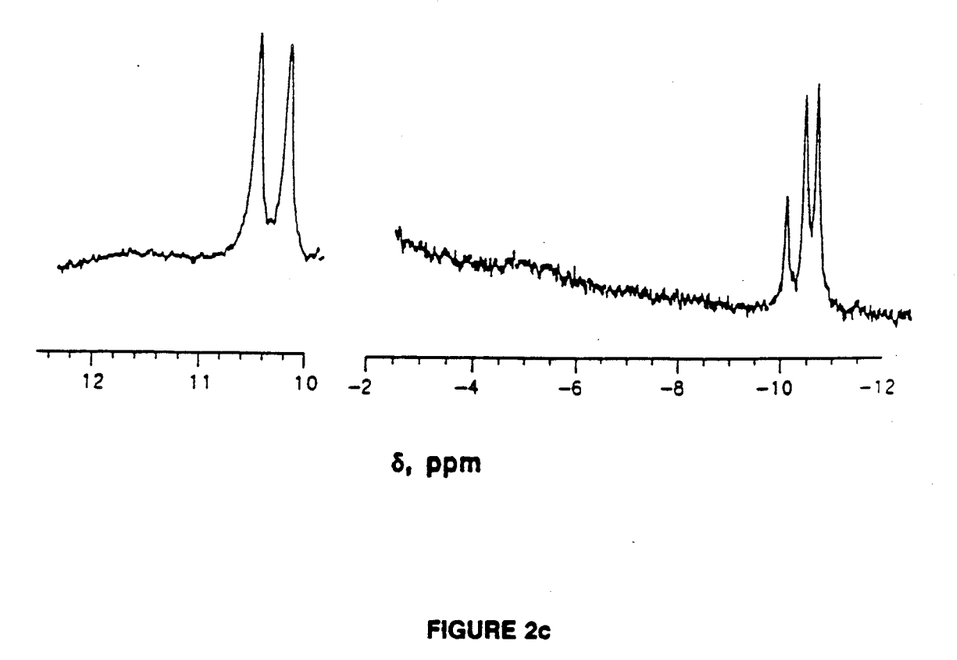

The solvent has a marked influence on the $^1$H-nmr spectrum observed for $SAP^{2+}$. Whereas both meso-H and pyrrolic N-H signals are sharp and well resolved in $CDCl^3$ solution, the corresponding signals in $CD_3CN$ and $CD_3OD$ solutions are broad and shifted (FIG. 2). In $CD_3CN$ solution, the meso-H resonances are observed at 10.65 and 10.36 ppm and the pyrrolic N-H resonances appear at −9.58, −9.93 and −0.16 ppm with the pattern changing to 1:2:2. In $CD_3OD$ solution, the meso-H signals appear as a very broad peak centered at ca. 11.1 ppm, and the pyrrolic N-H signals are lost due to rapid exchange with the solvent. These spectral changes are consistent with the $SAP^{2+}$ macrocycle existing as a monomer in $CDCl_3$(FIG. 2a) solution but as a dimer in $CD_3CN$ solution (Doughty, D. A.; Dwiggins Jr., C. W. *J. Phys. Chem.* 1969, 73, 423). Stacking of the macrocycle planes introduces strong $\pi,\pi$ interaction between adjacent rings which affects the ring currents and induces significant upfield shifts (Snyder, R. V.; La Mar, G. N. *J. Am. Chem. Soc.* 1977, 99, 7178). The observed change in the pattern of the pyrrolic N-H resonances (FIGS. 2a, 2b, and 2c) infers that the dimer possesses an ordered structure ((a) Abraham, R. J.; Eivazi, F.; Pearson, H.; Smith, K. M. *J. Chem. Soc., Chem. Commun.* 1976, 698, 699: (b) Abraham, R. J.; Barnett, G. H.; Hawkes, G. E.; Smith, K. M. *Tetrahedron* 1976, 32 2949: (c) Abraham, R. J.; Evans, B.; Smith, K. M. *Tetrahedron*

Figure 3:
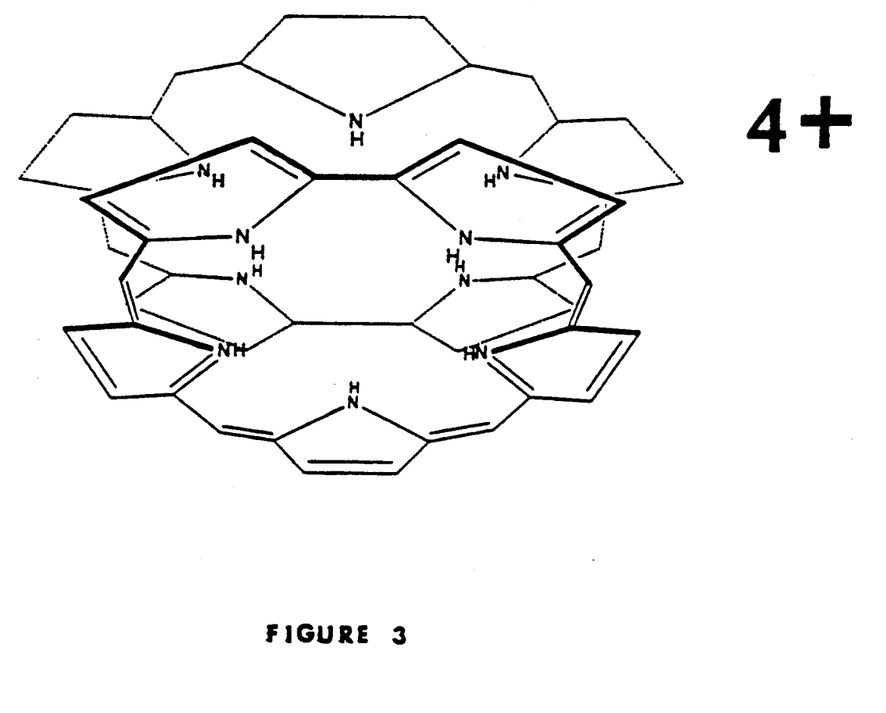
FIG. 3 shows the structure of the $SAP^{2+}$ ordered dimer formed in polar organic solvents, as inferred from nmr studies in $CD_3CN$ solution. The two pentapyrrolic macrocycles are held in an offset coplanar arrangement with an inter-planar separation of ca. 0.57 nm.

1978, 34, 1213) with the two macrocycles partially overlapping each other as shown in FIG. 3. For $SAP^{2+}$ in $CD_3OD$ solution, however, the spectra may be distorted by rapid exchange with the solvent such that the observed changes cannot be assigned unambiguously to dimerization of the macrocycle. Evidence from optical absorption spectra indicate, however, that $SAP^{2+}$ dimerizes at low concentration in both $CH_3CN$ and $CH_3OH$ solutions but not in $CHCl_3$.

Figure 4A:
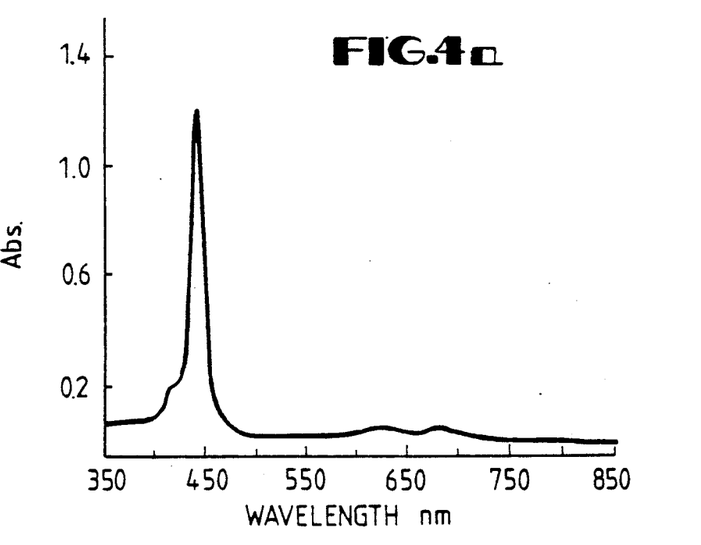
FIG. 4a shows the absorption spectra recorded for $SAP^{2+}$ ($5 \times 10^{-6}M$) in $CH_3CN$ solution.
Figure 4B:
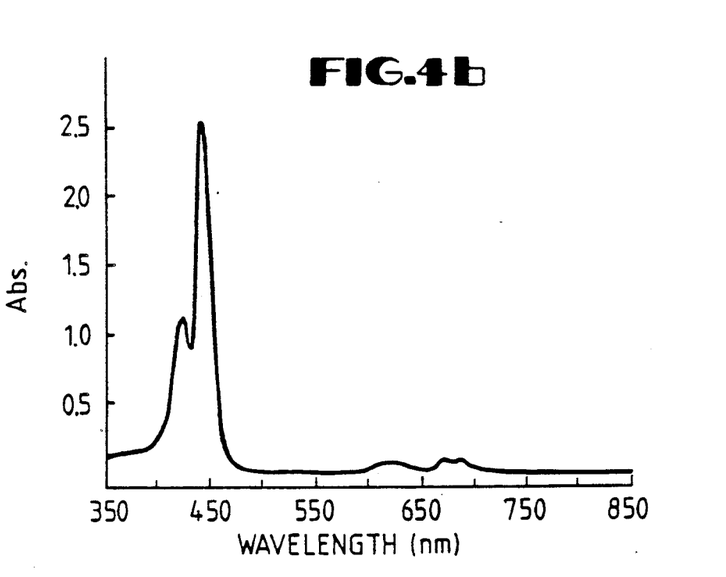
FIG 4b shows the absorption spectra recorded for $SAP^{2+}$ ($2 \times 10^{-5}M$) in $CH_3CN$ solution.
Figure 4C:
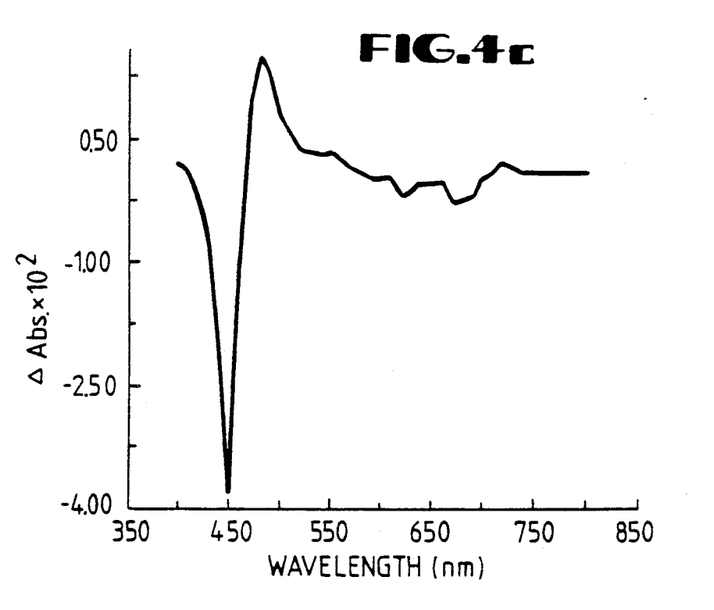
FIG. 4c shows the corresponding triplet state difference spectra for the $SAP^{2+}$ ($5 \times 10^{-6}M$) in $CH_3CN$ solution.
Figure 4D:
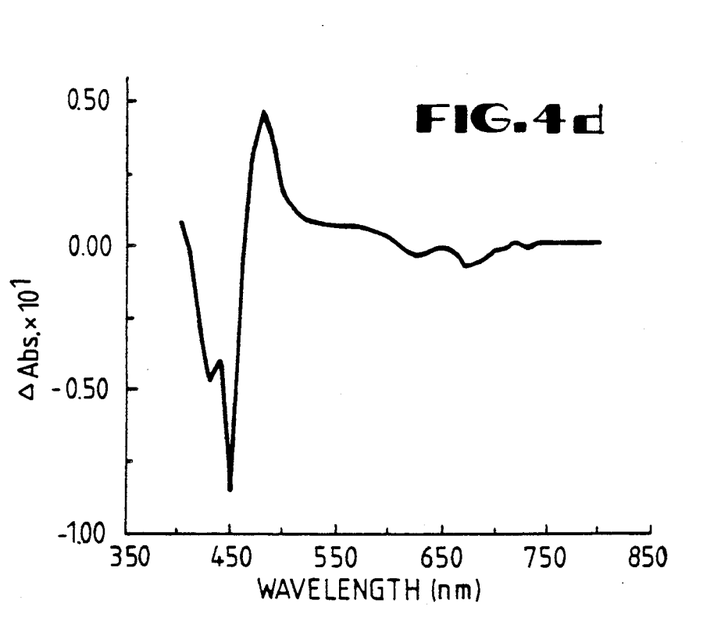
FIG. 4d shows the corresponding triplet difference spectra for $SAP^{2+}$ ($2 \times 10^{-5}M$) in $CH_3CN$ solution.

In dilute $CHCl_3$ solution, the optical absorption spectrum of $SAP^{2+}$ exhibits an intense Soret band at 456 nm (log $\epsilon = 5.65$) and two weaker Q-type bands at 624 (log $\epsilon = 4.26$) and 676 nm (log $\epsilon = 4.41$) (see FIGS. 4a and 4b). The spec quantitative agreement with that described by Bauer et al. (Bauer et al. J. Am. Chem. Soc. 1983, 105, 6429) for a related diprotonated sapphyrin derivative and it resembles spectra for other conjugate diacids derived from tetrapyrrolic macrocycles ((a) Austin, E.; Gouterman, M. Bioinorg. Chem. 1968, 90, 2735: (b) Harriman, A.; Richoux, M.-C. J. Photochem. 1984, 27, 205). The observed absorption spectrum is consistent with the high symmetry of the macrocycle and each of the three major bands is assigned to a $(\pi,\pi^*)$ transition. The compound was found to follow Beer's law over a wide concentration range $(0-10^{-3}M)$. Thus, in accordance with the nmr studies, $SAP^{2+}$ appears to exist in $CHCl_3$ solution in a monomeric form. The strong electrostatic repulsion between molecules will help to minimize aggregation of the macrocycle in nonpolar solvents. Because of the low polarity of the solvent, it is probable that extensive ion-pairing occurs between the $SAP^{2+}$ macrocycle and the two chloride counterions. Similar ion-pairing is known to occur in related diprotonated porphyrin conjugate diacids in non-polar solvents ((a) Austin, E.; Gouterman, M. Bioinorg. Chem 1968, 90, 2735: (b) Harriman, A.; Richoux, M.-C. J. Photochem. 1984, 27, 205).

In more polar solvents, $SAP^{2+}$ dimerizes at relatively low concentration. Beer's law is not obeyed in either $CH_3OH$ or $CH_3CN$ solutions and, following the treatment given by Pasternack (Pasternack, R. F. Ann. N.Y. Acad. Sci. 1973, 206, 614), dimerization constants of $(1.2\pm0.3)\times 10^4$ and $(1.5\pm0.3)\times 10^4$ $M^{-1}$, respectively derived in $CH_3OH$ and $CH_3CN$ solutions. Detailed analyses of these concentration dependent absorption profiles indicated that with concentrations of $SAP^{2+}$ below $1\times 10^{-3}$ M intermolecular association was restricted to dimerization (Pasternack, R. F. Ann. N.Y. Acad. Sci 1973, 206, 614). In $CH_3OH$ solution at very low concentration, there is a pronounced blue-shift in the Soret band (lambda=442 nm; log $\epsilon = 5.68$) together with a modest red-shift of $(4\pm1)$ nm in the Q-bands. These spectral shifts are not consistent with stabilization of $(\pi,\pi^*)$ transitions by the more polar solvent and, instead, they are attributed to increased dissociation of the salt in $CH_3OH$ solution. At higher concentration, the Soret band becomes broadened and the Q-bands are slightly red-shifted, although no new absorption bands appear.

Ion-pairing between macrocycle and counterion is expected to be less important in $CH_3CN$ than in $CHCl_3$ solution and, again, this is evidenced by the position of the Soret band at very low concentration (lambda=448 nm; log $\epsilon$5.65). In this solvent, increasing the concentration of $SAP^{2+}$ is accompanied by a slight red-shift (ca. 3 nm) in the two Q-bands and by a pronounced splitting of the Soret band (FIG. 4A, (a) and 4B(b). This splitting arises from strong exciton coupling (Gouterman, M.; Holten, D.; Lieberman, E. Chem. Phys. 1977, 25, 39) between the $\pi$-electron systems of stacked macrocyclic rings in a dimeric form of the compound. The nmr spectral shifts are in agreement with strong intermolecular $\pi,\pi$ interactions in $CH_3CN$ solution and, in addition, suggest the ordered structure displayed in FIG. 3. On this basis it is clear that intermolecular interaction between $SAP^{2+}$ molecules increases in the order $CHCl_3 < CH_3OH < CH_3CN$, as suggested also by nmr spectral shifts and from derived dimerization constants.

The strong intermolecular interaction found with high concentrations of $SAP^{2+}$ ($>10^{-5}$ M) in $CH_3CN$ solution corresponds to an exciton coupling energy (Gouterman, M.; Holten, D.; Lieberman, E. Chem. Phys. 1977, 25, 39), v of ca. 1055 $cm^{-1}$. Accepting an orthogonal structure for the dimer (FIG. 3), the interplanar separation distance is calculated to be $0.57\pm0.05$ nm (Gouterman, M.; Holten, D.; Lieberman, E. Chem. Phys. 1977, 25, 39). Similar splitting of the Soret band was observed for $SAP^{2+}$ molecules deposited on the surface of human serum albumin (v=880 $cm^{-1}$) and both negatively- (v=ca. 500 $cm^{-1}$) and positively-charged (v=1265 $cm^{-1}$) liposomes. The spectra observed in such cases were broader and much less well resolved than found in $CH_3CN$ solution and are assigned to aggregates rather than ordered dimers. It seems likely that such aggregated forms of $SAP^{2+}$ will abound under the in vivo conditions associated with photodynamic therapy and, consequently, it is important to determine the photodynamic properties of the aggregates as well as of the monomer and of the ordered dimer.

Photophysical Properties

The photophysical properties of $SAP^{2+}$ were determined in dilute $CHCl_3$ solution, where it is considered that the macrocycle exists as a monomer but with extensive ion-pairing with the $Cl^-$ counterions ((a) Austin, E.; Gouterman, M. Bioinorg. Chem. 1968, 90, 2735: (b) Harriman, A.; Richoux, M.-C. J. Photochem. 1984, 27, 205). Fluorescence emission can be detected readily; there is reasonably good mirror-symmetry with the Q-bands, good correlation between corrected excitation spectrum and ground-state absorption spectrum and a Stokes shift of 360 $cm^{-1}$. The fluorescence quantum yield ($\Phi_f$) is only $0.05\pm0.01$ and the excited singlet state lifetime ($\tau_s = 1.2\pm0.1$ ns) is short. The triplet excited state, which shows strong absorption at 460 nm ($\epsilon = 85,000\pm6,000$ $M^{-1} cm^{-1}$) is formed in appreciable yield ($\Phi_t = 0.54\pm0.06$) and has a relatively long lifetime ($\tau_t = 60\pm5$ $\mu s$) in $N_2$-saturated solution. However, internal conversion from the first excited singlet to the ground state accounts for ca. 40% of the overall photon balance. This rapid non-radiative process does not involve vibrational relaxation via the pyrrolic N-H bonds since exchanging these labile protons with $D^+$ ions does not affect the photophysical properties. Instead, the efficient internal conversion process is believed to arise, in part, from ion-pairing with the $Cl^-$ counterions, as found with phosphorus(V) porphyrins (Harriman, A. J. Photochem. 1983, 23, 37).

The triplet excited state is much shorter-lived than observed for the corresponding tetrapyrrolic macrocycles, possibly because of interaction with the halogenated solvent. Laser flash photolysis studies gave no indication of redox ion intermediates arising from electron transfer from triplet $SAP^{2+}$ to $CHCl_3$ but the halogen atoms can be expected to exert some spin-orbit coupling effect on the non-radiative deactivation process of the triplet state (McGlynn, S. P.; Azumi, T.; Kinoshita, M. "Molecular Spectroscopy of the Triplet State Prentice-Hall, New York, 1969). Despite any such perturbations, the triplet state reacts quantitatively with molecular oxygen upon aeration of the solution ($k_1 = 1.0 \pm 0.1 \times 10^9$ M$^{-1}$ s$^{-1}$).

$$(SAP^{2+})^* + O_2 \rightarrow SAP^{2+} + O_2(^1\Delta_g) \quad (1)$$

The quantum yield for formation of singlet molecular oxygen ($\Phi_\Delta$) formed from this reaction in CD$_2$Cl$_2$ solution was determined to be $0.28 \pm 0.07$. Thus, the triplet energy conversion efficiency is ca. 50%, which is low with respect to the corresponding porphyrins and phthalocyanines where conversion factors of ca. 75% are normal (This work does not address the aggregation state of the triplet species and it is possible that the dimer dissociates upon excitation into the singlet state).

Similar photophysical measurements were made in CH$_3$OH solution under conditions where SAP$^{2+}$ exists as an equilibrium mixture of monomer and dimer species. In very dilute solution, the monomer fluoresces at 685 nm, which corresponds to a Stokes shift of 280 cm$^{-1}$, with $\Phi_f = 0.06 \pm 0.02$ and possesses a singlet excited state lifetime of $2.7 \pm 0.3$ ns. Increasing the concentration of SAP$^{2+}$ results in a progressive decrease in fluorescence quantum yield and a red-shift in the peak maximum. The dimer fluorescence maximum occurs at 710 nm with $\Phi_f = 0.015 \pm 0.007$ and $\tau_s = 0.8 \pm 0.3$ ns. Thus, dimerization is accompanied by a red-shift in the fluorescence maximum of ca. 500 cm$^{-1}$ and a marked decrease in both fluorescence quantum yield and lifetime.

Under conditions of high dilution where the monomer species abounds, it was not possible to obtain accurate estimates for the quantum yields for formation of triplet state or O$_2$($^1\Delta_g$). At higher concentration of SAP$^{2+}$ in N$_2$-saturated CH$_3$OH solution ([SAP$^{2+}$]$=9 \times 10^{-5}$ M) where the dimer accounts for approximately 65 and 45% of the total absorbance at 355 and 532 nm respectively, excitation of the monomer/dimer mixture resulted in formation of a triplet species (This work does not address the aggregation state of the triplet species and it is possible that the dimer dissociates upon excitation into the singlet state) which decayed via first-order kinetics with $\tau_t = 80 \pm 5$ $\mu$s. Upon aeration of the solution, the triplet state reacted quantitatively with molecular oxygen ($k_1 = 3.0 \pm 1.0 \times 10^9$ M$^{-1}$ s$^{-1}$) and, in CD$_3$OD solution, produced O$_2$($^1\Delta_g$) with a quantum yield of $0.13 \pm 0.04$.

The fluorescence properties of SAP$^{2+}$ in CH$_3$CN are similar to those described above for CH$_3$OH solution. Thus, the monomer species fluoresces at 680 nm with $\Phi_f = 0.07 \pm 0.02$ and $\tau_s = 2.8 \pm 0.3$ ns whereas the d fluoresces at 710 nm with $\tau_f = 0.020 \pm 0.008$ and $\tau_s = 0.8 \pm 0.2$ ns. As seen from FIG. 4B($b$), the triplet difference absorption spectral profile in the Soret region depends strongly upon the concentration of SAP$^{2+}$. The differences appear to relate to changes in the ground state absorption spectrum due to exciton coupling effects associated with dimerization. In very dilute solution, where the ground state monomer accounts for more than 95% of the total absorbance at both 355 and 532 nm, the triplet difference spectrum shows an intense absorption maximum at 480 nm ($\epsilon_t = 78,000 \pm 9,000$ M$^{-1}$ cm$^{-1}$). Under these conditions, the triplet state ($\Phi_t = 0.35 \pm 0.05$) is formed in lower yield than observed for the ion-pair species in CHCl$_3$ solution although the triplet lifetime ($\tau_t = 50 \pm 10$ $\mu$s) remains similar. In dilute CD$_3$CN solution, the triplet reacts with molecular oxygen ($k_1 = 2.0 \pm 0.5 \times 10^9$ M$^{-1}$ s$^{-1}$) to produce O$_2$($^1\Delta_g$) with a quantum yield of $0.19 \pm 0.06$.

In CH$_3$CN solution, the dimer exhibits a much higher molar extinction coefficient at 355 nm than does the monomer species whereas the values are comparable at 532 nm. At high concentrations of SAP$^{2+}$ ([SAP$^{2+}$]$= 1 \times 10^{-4}$ M) in CH$_3$CN solution, incident photons from laser excitation at 35 nm are absorbed preferentially (ca. 90%) by the ground state dimer. Under such conditions in O$_2$-saturated CD$_3$CN solution, generation of O$_2$($^1\Delta_g$) occurred with a quantum yield of $0.17 \pm 0.05$. Excitation at 355 nm in N$_2$-saturated CH$_3$CN solution produces the triplet state (This work does not address the aggregation state of the triplet species and it is possible that the dimer dissociates upon excitation into the singlet state) which decays at the same rate as observed for the triplet in dilute solution. At high laser intensities conversion of the ground state into the triplet manifold is not quite complete, because of the high concentration needed to produce extensive dimerization, and the triplet difference molar extinction coefficient at 480 nm was derived by extrapolation to be $52,000 \pm 9,000$ M$^{-1}$ cm$^{-1}$. Using this value, the quantum yield for formation of the triplet manifold upon excitation of the ground state dimer was determined to be $0.39 \pm 0.10$. Thus, the efficiency with which the triplet state produces singlet oxygen (ca. 45%) observed for excitation of the ground state dimer approaches that found for excitation of the corresponding monomer species in both CD$_3$CN (55%) and CDCl$_3$ (50%) solutions.

The photophysical measurements were extended to include studies of SAP$^{2+}$ bound to the surface of human serum albumin and to both negatively- and positively-charged liposomes. In each case, extensive aggregation of the macrocycle was apparent from optical absorption and emission spectra. Although quantitative measurements were restricted by the high levels of light scattering inherent with such samples, laser flash photolysis studies showed that these aggregates gave extremely low quantum yields for triplet state formation and for subsequent production of O$_2$($^1\Delta_g$). Indeed, the photophysics of such aggregated forms of SAP$^{2+}$ are dominated by efficient internal conversion and the aggregates are poor triplet state photosensitizers.

The references cited herein are incorporated for the reasons cited.

Changes in the construction, operation, and arrangement of the various elements, steps and procedures described herein without departing from the concept and scope of the invention as defined in the following claims.

We claim:

1. A method of producing singlet oxygen, comprising:
   dissolving a diprotonated sapphyrin conjugate diacid in a solvent;
   exciting said diprotonated sapphyrin conjugate diacid at an absorbing wavelength to form a triplet species; and
   generating singlet oxygen by reacting molecular oxygen with said triplet species.

2. The method of claim 1 wherein the sapphyrin compound is an alkylated diprotonated sapphyrin conjugate diacid.

3. The method of claim 1 wherein the diprotonated sapphyrin conjugate diacid is diprotonated 3,8,12,13,17,22-hexaethyl-2,7,18,23-tetramethylsapphyrin.

4. The method of claim 1 wherein the solvent is an organic solvent.

5. The method of claim 1 wherein the exciting wavelength is in the visible range.

6. The method of claim 1 wherein the exciting wavelength is between about 450 nm and about 600 nm.

7. The method of claim 4 wherein the organic solvent is characterized as being of low polarity.

8. The method of claim 4 wherein the organic solvent is characterized as having high polarity.

9. The method of claim 1 wherein the excitation is produced by photons from a laser.

10. A method of selective production of singlet oxygen, comprising:
   incorporating a diprotonated sapphyrin conjugate diacid into a suitable biological carrier in an aqueous environment;
   illuminating said aqueous environment at a wavelength effective to excite said diprotonated sapphyrin conjugate diacid to triplet state species;
   generating singlet oxygen by allowing molecular oxygen dissolved in said environment to react with said triplet state species; and
   terminating said singlet oxygen generation by cessation of said illumination.

11. The method of claim 10 wherein the biological carrier is a positively or negatively charged liposome.

12. The method of claim 10 wherein the biological carrier is a membranous vesicle.

13. A method of modulating production of singlet oxygen in organic solvents, comprising:
   dissolving a diprotonated sapphyrin conjugate diacid in an organic solvent to form a solution;
   introducing molecular oxygen into said solution;
   illuminating said solution sufficiently to cause excitation of said diprotonated sapphyrin conjugate diacid to excited triplet species; and
   adding at least one moderator to said solution, said moderator comprising ampholytic biologically compatible materials to which said sapphyrin compound will bind.

14. The method of claim 13 wherein the moderator is a protein.

15. The method of claim 13 wherein the moderator is albumin.

16. The method of claim 13 wherein the moderator is a membranous material.

17. The method of claim 13 wherein the moderator is a positively or negatively charged liposome.

18. The method of claim 13 wherein the organic solvent is selected from a group consisting of chloroform, methanol, and acetonitrile.

* * * * *

UNITED STATES PATENT AND TRADEMARK OFFICE
CERTIFICATE OF CORRECTION

PATENT NO. : 5,120,411
DATED : June 9, 1992
INVENTOR(S) : Sessler et al

It is certified that error appears in the above-indentified patent and that said Letters Patent is hereby corrected as shown below:

In column 1, line 8, before BACKGROUND OF THE INVENTION insert a new paragraph:

--This invention was made in part with government support under the National Science Foundation Presidential Young Investigator Award (1986) to J.L. Sessler, grant CHE-8552768. The government has certain rights in the invention.--

Signed and Sealed this

Fourteenth Day of September, 1993

*Attest:*

BRUCE LEHMAN

*Attesting Officer*  *Commissioner of Patents and Trademarks*